United States Patent [19]

MacKay et al.

[11] 4,121,922

[45] Oct. 24, 1978

[54] METHOD AND APPARATUS FOR MEASURING PERCENTAGE REDUCTION IN A METAL ORE REDUCTION REACTOR

[75] Inventors: Patrick W. MacKay; Enrique Martínez Vera; Ramón de la Peña, all of Monterrey, Mexico

[73] Assignee: Fierro Esponja, S.A., Monterrey, Mexico

[21] Appl. No.: 751,997

[22] Filed: Dec. 17, 1976

Related U.S. Application Data

[63] Continuation-in-part of Ser. No. 698,001, Jun. 21, 1976, abandoned.

[51] Int. Cl.$^2$ ............................................. C21B 13/02
[52] U.S. Cl. ......................................... 75/34; 266/80; 422/83; 23/232 R
[58] Field of Search ................. 75/34, 35, 60; 266/80; 23/230 A, 253 A

[56] References Cited

U.S. PATENT DOCUMENTS

| | | | |
|---|---|---|---|
| 3,157,488 | 11/1964 | Taylor | 75/34 |
| 3,304,170 | 2/1967 | Hinsvark | 75/34 |
| 3,423,201 | 1/1969 | Celada et al. | 75/35 |
| 3,489,518 | 1/1970 | Revell et al. | 23/230 A |
| 3,522,035 | 7/1970 | Putman | 75/60 |
| 3,528,800 | 9/1970 | Blum et al. | 75/60 |
| 3,601,381 | 8/1971 | Beggs | 266/80 |

*Primary Examiner*—M. J. Andrews
*Attorney, Agent, or Firm*—Curtis, Morris & Safford

[57] ABSTRACT

A method and apparatus for measuring the percentage reduction of iron ore in a reduction reactor of a multiple reactor gaseous reduction system. In accordance with a preferred embodiment, the flow and composition of the reducing gas fed to the reduction reactor and the flow and composition of the reactor effluent gas after cooling are measured and the measurements are fed to a computer along with data on the initial weight of the charge to the reactor, the moisture content of the charge and the initial reducible oxygen in the charge. The computer is programmed to compute the rate of oxygen removal from the charge, integrate the rate of removal with respect to time and compare the integral with the initial oxygen content of the charge to evaluate percentage reduction thereof.

21 Claims, 1 Drawing Figure

METHOD AND APPARATUS FOR MEASURING PERCENTAGE REDUCTION IN A METAL ORE REDUCTION REACTOR

This application is a continuation-in-part of application Ser. No. 698,001 filed June 21, 1976 now abandoned.

This invention relates to the batchwise gaseous reduction of metal oxide ores in a multi-stage gaseous reduction system of the type in which separate bodies of metal-bearing material are simultaneously treated in a plurality of reactors to produce sponge metal. More particularly, the invention relates to a novel method and apparatus for measuring the percentage reduction that has occurred in a bed of metal-bearing material in a reduction reactor of such a system. The invention will be illustratively described in connection with the reduction of iron ore to produce sponge iron, although as the description proceeds, it will become apparent that the invention can equally well be used in the reduction of other oxidic ores, e.g., those of nickel, copper and tin.

Typical gaseous reduction systems in which the present invention may be usefully employed are disclosed in U.S. Pat. Nos. 2,900,247; 3,423,201; 3,890,142; and 3,904.397. Reduction systems of the type shown in these patents are essentially batch systems commonly comprising a cooling reactor and two reduction reactors containing fixed beds of iron-bearing material, and a fourth reactor from which sponge iron is discharged and which is charged with fresh ore while the cooling and reduction steps are being carried out in the other reactors of the system. At the end of a cycle of operations the reactors are functionally interchanged to cause the first stage reduction reactor to become the second stage reduction reactor, the second stage reduction reactor to become the cooling reactor, the cooling reactor to become the re-charging reactor and the re-charging reactor to become the first stage reduction reactor.

The ore is reduced in the reduction reactors and sponge iron is simultaneously cooled in the cooling reactor by passing a reducing gas in sequence through the beds of iron-bearing material in the reactors. Typically the reducing gas, which is largely composed of carbon monoxide and hydrogen and contains minor amounts of methane and carbon dioxide, is passed first through a cooling reactor of the system and then in sequence through a second stage reduction reactor and a first stage reduction reactor. Desirably the effluent gas from each reactor is cooled to remove water therefrom and in the case of the reduction reactors, reheated to an elevated temperature before entering the reactor. The reducing gas can be conveniently prepared by catalytic reformation of a mixture of steam and natural gas in a heated catalytic reformer in known manner.

In one of its aspects the present invention is concerned with the problem of providing a continuous measurement of the extent to which reduction of the iron ore has occurred in one or more reduction reactors of such a system. Such a determination is useful in enabling the plant operator to better determine when a given cycle of operations has been completed and a new cooling and reduction cycle should be initiated.

During the passage of the reducing gas through the bed of iron-bearing material in a reduction reactor of the system, the composition of the gas changes as an incident of the removal of oxygen from the iron ore and hence it is theoretically possible to determine the extent to which reduction of the ore has occurred by measuring changes in gas composition. However, when an effort is made to so measure percentage reduction, a number of practical problems are encountered. In the first place, the constituents of the reducing gas react with the oxygen of the iron ore by a plurality of reactions that, in general, are reversible and have temperature dependent equilibria. Thus a rather complex series of changes occurs within the reducing zone of the reactor. While apparatus is commercially available for rapidly and continuously measuring most of the constituents of the reducing gas, i.e., carbon monoxide, hydrogen, methane and carbon dioxide, the accurate measurement of water vapor in the reducing gas presents a problem, particularly in those systems wherein the effluent gas from the reduction reactor is cooled and dewatered in a quenching tower by direct contact with cooling water.

A further problem encountered arises out of the fact that the effluent gas from the reactor contains a considerable amount of suspended dust. This dust tends to interfere with the accurate measurement of the flow and composition of the gas.

It is accordingly an object of the present invention to provide a novel method and apparatus for measuring the percentage reduction of an oxidic ore in a fixed bed reduction reactor. It is another object of the invention to provide a novel method and apparatus for obtaining a continuous measurement of the extent to which reduction has occurred since the beginning of a reduction cycle in one or more fixed bed reduction reactors of a gaseous iron are reduction system of the type referred to above. Other objects of the invention will be in part obvious and in part pointed out hereafter.

The objects and advantages of the present invention are achieved in general by measuring the flow and composition of the reducing gas flowing to a reduction reactor before the gas is heated and fed to the reactor, measuring the composition, and in some cases the flow, of the effluent reducing gas from a reactor after it has been quench cooled, and correlating these flow and composition measurements with the initial oxygen content of the iron-bearing bed within the reactor to determine the extent to which reduction of the iron ore has occurred.

As indicated above, it does not appear to be possible to obtain an accurate determination of percentage reduction by using a conventional material balance technique because of the difficulty of obtaining an accurate measurement of the change in the water content of the gas flowing through the reduction reactor. The effluent gas from the reactor flows to a quench cooler wherein it is rapidly cooled and de-watered by a direct contact with cooling water. The quench cooler also serves to remove a considerable amount of dust present in the reduction reactor effluent gas. If a sample is taken between the reactor and the cooler, the dust present in the gas stream makes it difficult to determine accurately the composition and water vapor content of the gas. On the other hand, if a sample is taken of the cooler effluent gas, the gas composition will differ from the composition of the reactor effluent gas by the amount of water that has been removed from the gas stream in the quench cooler. Since this removed water is commingled with a much larger quantity of cooling water, it cannot be accurately measured.

In accordance with a first embodiment of the method of the invention, this problem is circumvented by determining the flow and composition of the reactor feed gas before it is heated and fed to the reactor, determining the flow and composition of the reactor effluent gas after it has been cooled and de-watered and correlating the measured values of these flows and compositions to determine the rate of oxygen removal from the bed of iron-bearing material in the reactor. The rate of oxygen removal can then be integrated to provide a signal continuously indicative of the percentage reduction of the ore. As will be more fully pointed out hereafter, it is possible by using a combination of a hydrogen balance and an oxygen balance to obtain an acceptable determination of oxygen removal from the ore in the reduction reactor without making any measurement of the change in the amount of water vapor in the gas.

In accordance with a second embodiment of the present method the flow and composition of the reactor feed gas are determined, but no flow measurement of the effluent gas is made; only the composition of the effluent gas is determined. In accordance with this embodiment the measurement of the flow of reactor effluent gas can be omitted by using a combination of three material balances, namely, a hydrogen balance, an oxygen balance and a carbon balance, to determine the rate of removal of oxygen from the ore.

In general the first embodiment is desirably used where the operating conditions of the reduction reactor and/or the composition of the feed gas are such that carburization of the iron-bearing material is likely to occur, whereas the second embodiment is desirably used when the operating conditions in the reactor and the composition of the feed gas are such that there is little likelihood that the carbon content of the feed gas will change as it passes through the reactor. Since the first embodiment of the invention is the more general embodiment, it will be described first.

The objects and advantages of the invention can best be understood and appreciated by reference to the accompanying drawing which illustrates diagrammatically a preferred embodiment of the apparatus of the invention particularly adapted to be used in carrying out the first embodiment of the method of the invention. More particularly, the drawing illustrates a reduction reactor of a gaseous iron ore reduction system of the type disclosed, for example, in U.S. Pat. No. 3,423,201. The reactor may contain a bed of partially reduced iron ore or a bed of iron ore to be reduced and is provided with apparatus for continuously measuring the extent to which the body of iron-bearing material in the bed has been reduced, i.e., the average percentage reduction in the bed.

Figure 1:
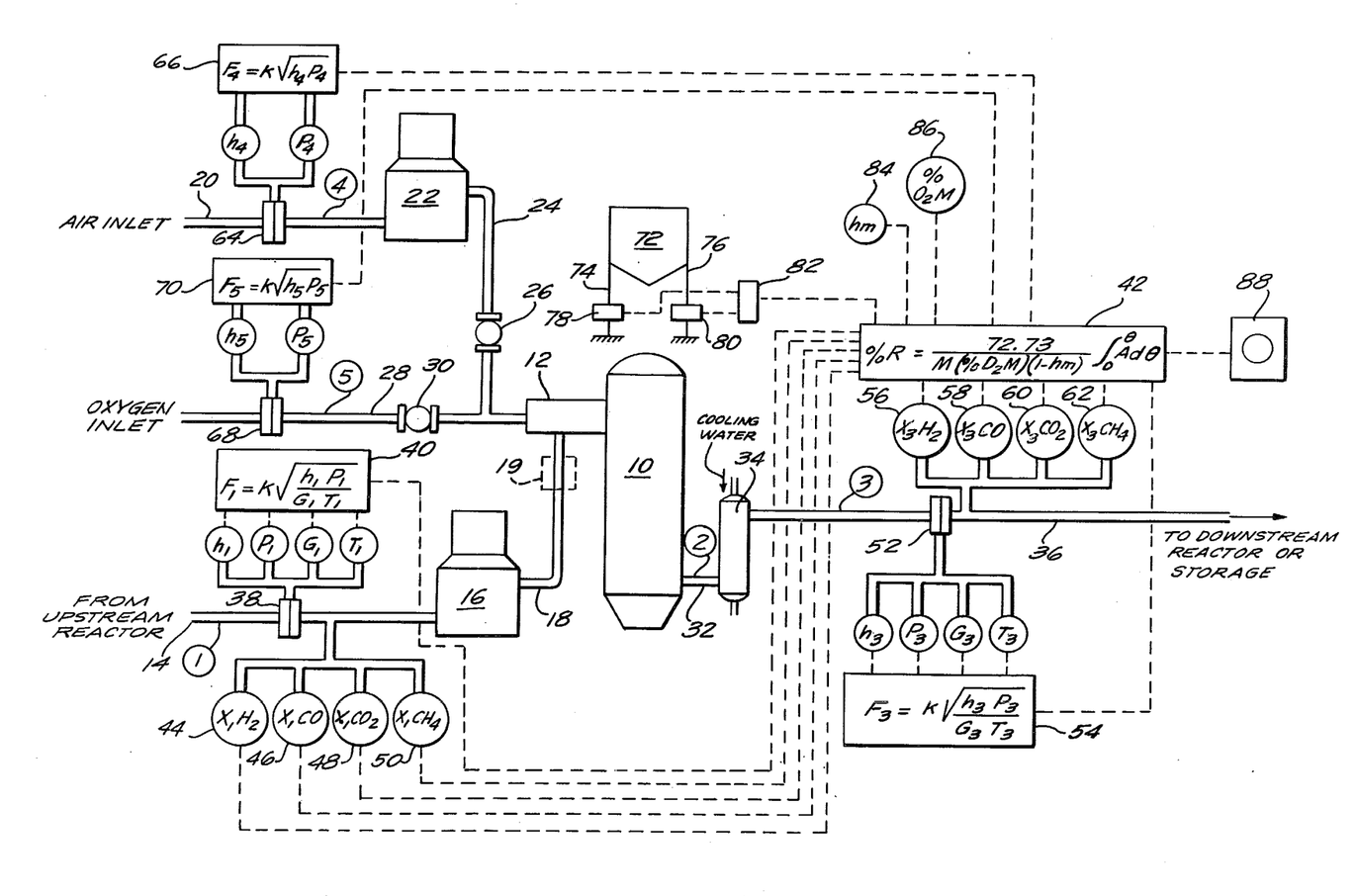

Referring to the drawing, the numeral 10 designates a reduction reactor that corresponds generally to one of the reactors of the reduction system of U.S. Pat. No. 3,423,201 and that is provided with a combustion chamber 12 communicating with the interior thereof. As disclosed in U.S. Pat. No. 3,423,201 and outlined above, multiple batch reactor systems of the type with which the present invention is especially useful commonly comprise four reactors operated in a cyclic manner with each reactor of the system used successively as a first reduction stage reactor, a second reduction stage reactor, a cooling reactor and a discharging and charging reactor. In systems comprising three or more reduction reactors, each reactor is used to carry out three or more reduction stages. The method and apparatus of the invention are adapted to be used to determine and indicate the percentage reduction in a reactor of such a system during the time interval that it performs a reducing function, e.g., during the first and second stage reduction periods when using a 4-reactor system or during the three reduction stages used in a 5-reactor system. In the following description it will be assumed that reactor 10 is part of a 4-reactor system.

Referring to the left-hand side of the drawing, reducing gas from an upstream reactor of the system (which may be either a cooling reactor or another reduction reactor) flows through a pipe 14 to a heater 16 wherein it is heated to a temperature of say 700° to 800° C. From heater 16 the gas flows through pipe 18 to the combustion chamber 12 which may be of the type described in U.S. Pat. No. 2,900,247. As disclosed in that patent, the gas flowing to the combustion chamber is mixed with a minor amount of oxygen-containing gas and partially burned to form a mixture at a still higher temperature of say 750° to 900° C. From combustion chamber 12 the hot gas flows into the reactor and downwardly through the bed of iron-bearing material therein.

As indicated in the drawing, the effluent gas from heater 16 may be passed through a superheater 19 to raise its temperature to the desired reducing temperature, in which event the combustion chamber 12 can be dispensed with.

The oxygen-containing gas mixed with the reducing gas in combustion chamber 12 may be either air or oxygen or a mixture of air and oxygen. Referring to the upper left-hand portion of the drawing, air can be supplied to the combustion chamber through a pipe 20 connected to a heater 22 wherein the air is preheated to an elevated temperature, e.g., 700° C. From the heater 22 the heated air flows through a pipe 24 containing a valve 26 to the combustion chamber 12. If oxygen is used instead of or in addition to air, the oxygen need not be preheated. Thus oxygen may be supplied to the system through a pipe 28 that contains a shut-off valve 30 and is connected to pipe 24 which in turn leads to combustion chamber 12.

After flowing through the bed of partially reduced ore in the reactor 10, the gas leaves the reactor through pipe 32 and flows to and through a quench cooler 34 wherein it is cooled and de-watered and dust is removed therefrom. From quench cooler 34 the cooled gas flows through pipe 36 to a downstream reactor or to a suitable point of storage or use as a fuel gas.

In describing the apparatus used to determine the percentage reduction, reference will be made to the gas composition at five different locations designated as "1" to "5" in the drawing. Location "1" is the pipe 14 through which reducing gas from the cooling reactors flows to the heater 16 of the reduction chamber 10; location "2" is the pipe 32 between reactor 10 and cooler 34; location "3" is the pipe 36 carrying effluent gas from the cooler 34; location "4" is the pipe 20 through which air flows to the air heater 22; location "5" is pipe 28 through which oxygen flows to the combustion chamber 12 of reactor 10.

At location "1" there is an orifice 38 forming part of an orifice flowmeter 40. The differential pressure across the orifice 38 and the pressure, temperature and specific gravity of the gas flowing through pipe 14 are measured and correlated in meter 40 to produce a signal proportional to the gas flow rate at location "1" which signal is transmitted to a computer 42. As indicated in the drawing, the flow is determined by correlating the differential pressure across orifice 38 with the pressure, temperature and specific gravity of the gas flowing through pipe 14 in accordance with the standard flow formula $$F = K\sqrt{\frac{hP}{GT}}$$

wherein:
- $h$ = differential pressure head across orifice
- $P$ = static absolute pressure at the orifice
- $G$ = specific gravity of gas relative to air
- $T$ = absolute temperature of gas at orifice
- $K$ = orifice constant corrected to give dry gas flow rate
- $F$ = molar flow rate Also the gas composition at location "1" is determined by a series of analytical devices 44 through 50. More particularly, the hydrogen content of the gas expressed as the mole fraction of hydrogen $X_{1H_2}$ is determined in analytical device 44, the carbon monoxide content of the gas expressed as the mole fraction of carbon monoxide $X_{1CO}$ is determined in analytical device 46, the carbon dioxide content of the gas expressed as the mole fraction of carbon dioxide $X_{1CO_2}$ is determined in analytical device 48, and the methane content of the gas expressed as the mole fraction of methane $X_{1CH_4}$ is determined in analytical device 50. Each of the analytical devices produces a signal which is a function of the proportion of the particular component in the gas stream at location "1" and this signal is transmitted to the computer 42.

The gas composition and gas flow rate at location "3" are measured in a similar fashion. More particularly, an orifice 52 is provided in pipe 36 and cooperates with an orifice meter 54 responsive to the differential pressure across the orifice, as well as to the pressure, temperature and specific gravity of the gas flowing through pipe 36 to generate a signal which is a function of the gas flow rate and that is transmitted to the computer 42. Gas analysis devices 56 through 62 are provided to determine, respectively, the hydrogen mole fraction $X_{3H_2}$, carbon monoxide mole fraction $X_{3CO}$, carbon dioxide mole fraction $X_{3CO_2}$, and methane mole fraction $X_{3CH_4}$ of the gas flowing through pipe 36. The analysis devices produce signals corresponding to the mole fraction of the several gas components, which signals are transmitted to the computer 42 as indicated in the drawing. At location "4" there is an orifice 64 in the pipe 20 which cooperates with an orifice meter 66 responsive to the differential pressure across orifice 64, as well as to the pressure of the gas flowing through pipe 20 to generate a signal which is a function of the flow of air to the combustion chamber 12. The signal generated by the meter 66 is transmitted to the computer 42. Since the gas flowing through pipe 20 is atmospheric air, only the differential pressure across orifice 64 and the pressure of the flowing gas need be measured; the specific gravity and temperature may be considered constant. Also since atmospheric air has a constant composition, no analytical devices are required to determine the composition of the gas flowing through pipe 20. As indicated in the drawing, the flow of air through pipe 20 as measured by orifice meter 66 is designated by the symbol "$F_4$" and will be so designated in the following discussion.

The rate of flow of oxygen through pipe 28 at location "5" is determined by an orifice 68 in pipe 28 and cooperating orifice meter 70. The meter 70 is responsive to the differential pressure across orifice 68, as well as to the static pressure in pipe 28 and correlates the measured values to generate a signal which is a function of the oxygen flow $F_5$ at location "5". The signal thus generated is transmitted to the computer 42.

Located above the reactor 10 there is a charging hopper 72 supported on the legs 74 and 76 containing the load measuring devices 78 and 80, respectively. In practice three or more legs would be provided to ensure stability. The load measuring devices 78 and 80 may be, for example, strain gauges which have resistances that vary as a function of the load carried by legs 74 and 76 and which are connected to a resistance measuring device 82 that generates a signal which is a function of the weight of hopper 72 and its contents and transmits the signal to computer 42. The hopper 72 is charged with a proper quantity of ore to provide a desired charge in reactor 10 and a signal representing the weight of the charge is transmitted to computer 42 after which the charge is introduced into the reactor 10 for the initial reduction cycle. The initial reducible oxygen constant and humidity of the ore are constants in respect to any particular charge. These values are measured and as indicated at 84 and 86 in the drawing, values indicating the magnitudes of the moisture content and initial reducible oxygen content of the ore are introduced into the computer.

Within the computer 42 the signals representing the flow and composition of the gas at location "1", the flow and composition of the gas at location "3", the flow of air at location "4" if air is used, the flow of oxygen at location "5" if oxygen is used, the weight of iron ore in the charge, the initial percentage of reducible oxygen in the charge, and the humidity of the charge are correlated to generate a signal representative of the percentage reduction of the ore and this signal is transmitted to an indicating recorder 88. The record thus made can be used by the operator as a basis for determining when the desired percentage reduction of the ore has occurred. While the gas flow rates and compositions at locations "1" to "5" can be correlated with the initial reducible oxygen content of the ore, the weight of ore charged, and the humidity of the ore in various ways to determine percentage reduction, a preferred method of correlating these measurements will now be described.

In the following discussion the symbols listed below have the indicated meanings, with the gas flow being expressed in moles. Also the gas flow is on a dry basis, except for the flow of water vapor.

- $F_1$ = total gas flow at location "1"
- $F_{1H_2}$ = flow of hydrogen at location "1"
- $F_{1CO}$ = flow of carbon monoxide at location "1"
- $F_{1CO_2}$ = flow of carbon dioxide at location "1"
- $F_{1CH_4}$ = flow of methane at location "1"
- $F_{1H_2O}$ = flow of water vapor at location "1"
- $F_{2CO}$ = flow of carbon monoxide at location "2"
- $F_{2CO_2}$ = flow of carbon dioxide at location "2"
- $F_{2H_2O}$ = flow of water vapor at location "2"
- $F_3$ = total flow of gas at location "3"
- $F_{3H_2}$ = flow of hydrogen at location "3"
- $F_{3CO}$ = flow of carbon monoxide at location "3"
- $F_{3CO_2}$ = flow of carbon dioxide at location "3"
- $F_{3CH_4}$ = flow of methane at location "3"
- $F_{3H_2O}$ = flow of water vapor at location "3"
- $F_W$ = water removed in cooler 34, moles/unit time
- $F_4$ = flow of air to combustion chamber 12
- $F_5$ = flow of oxygen to combustion chamber 12

R = percent reduction of the ore
$(O_2)i$ = initial oxygen content of ore (a constant) lb.-moles
$(O_2)r$ = oxygen removed from ore (a variable) lb.-moles
M = metric tons of ore charged to reactor
$O_{2m}$ = weight percent of reducible oxygen in the ore
$h_m$ = humidity weight fraction of the ore
$F_{O_{2m}}$ = rate of oxygen removal from the ore
$0.21F_4$ = flow of oxygen in the air fed to the combustion chamber
$\theta$ = elapsed time since beginning of first stage reduction The formula for $F_{O_{2m}}$ representing the rate at which oxygen is removed from the ore can be derived as follows:

By an elemental hydrogen ($H_2$) balance between locations "1" and "3" one obtains:

$$F_{1H_2} + 2F_{1CH_4} + F_{1H_2O} = F_{3H_2} 3 0 2F_{3CH_4} + F_{3H_2O} + Fw \quad (1)$$

Solving for Fw gives:

$$Fw = (F_{1H_2} - F_{3H_2}) + 2(F_{1CH_4} - F_{3CH_4}) + (F_{1H_2O} - F_{3H_2O}) \quad (2)$$

By an elemental oxygen ($O_2$) balance between locations "1" and "2" one obtains:

$$\tfrac{1}{2} F_{1CO} + F_{1CO_2} + \tfrac{1}{2} F_{1H_2O} + 0.21 F_4 + F_5 + F_{O_{2m}} = \tfrac{1}{2} F_{2CO} + F_{2CO_2} + \tfrac{1}{2} F_{2H_2O} \quad (3)$$

Multiplying by 2 gives:

$$F_{1CO} + 2F_{1CO_2} + F_{1H_2O} + 0.42 F_4 + 2F_5 + 2F_{O_{2m}} = F_{2CO} + 2F_{2CO_2} + F_{2H_2O} \quad (4)$$

Solving equation (4) for $F_{O_{2m}}$ gives:

$$F_{O_m} = \tfrac{1}{2} [(F_{2CO} - F_{1CO}) + 2(F_{2CO_2} - F_{1CO_2}) + (F_{2H_2O} - F_{1H_2O}) - 0.42 F_4 - 2F_5] \quad (5)$$

By a material balance of water between locations "2" and "3":

$$F_{2H_2O} = F_{3H_2O} + Fw \quad (6)$$

Substituting the expression for $F_{2H_2O}$ of equation (6) into equation (5):

$$F_{O_{2m}} = \tfrac{1}{2}[(F_{2CO} - F_{1CO}) + 2(F_{2CO_2} - F_{1CO_2}) + (F_{3H_2O} + Fw - F_{1H_2O}) - 0.42 F_4 - 2F_5] \quad (7)$$

Substituting the expression for Fw from equation (2) into equation (7) gives:

$$F_{O_{2m}} = \tfrac{1}{2}[(F_{2CO} - F_{1CO}) + 2(F_{2CO_2} - F_{1CO_2}) + (F_{3H_2O} - F_{1H_2O}) + (F_{1H_2} - F_{3H_2}) + 2(F_{1CH_4} - F_{3CH_4}) + (F_{1H_2O} - F_{3H_2O}) - 0.42 F_4 - 2F_5] \quad (8)$$

The terms $F_{1H_2O}$ and $F_{3H_2O}$ in equation (8) may be cancelled to give:

$$F_{O_{2m}} = \tfrac{1}{2} [(F_{1H_2} - F_{3H_2}) + 2(F_{1CH_4} - F_{3CH_4}) - (F_{1CO} - F_{2CO}) - 2(F_{1CO_2} - F_{2CO_2}) - 0.42 F_4 - 2F_5] \quad (9)$$

It is evident that:

$$F_{2CO} = F_{3CO} \text{ and } F_{2CO_2} = F_{3CO_2}$$

Hence by substituting $F_{3CO}$ for $F_{2CO}$ and $F_{3CO_2}$ for $F_{2CO_2}$ all terms containing $F_2$ can be eliminated to give:

$$F_{O_{2m}} = \tfrac{1}{2}[(F_{1H_2} - F_{3H_2}) + 2(F_{1CH_4} - F_{3CH_4}) - (F_{1CO} - F_{3CO}) - 2(F_{1CO_2} - F_{3CO_2}) - 0.42 F_4 - 2F_5] \quad (10)$$

Equation (10) is a general expression which can be used to determine the rate of removal of oxygen from the ore for four different modes of feeding oxygen-containing gas to the combustion chamber, namely, air alone ($F_5$ is zero), oxygen ($F_4$ is zero), a mixture of air and oxygen, or no addition of oxygen-containing gas ($F_4$ and $F_5$ are both zero).

If X is used to represent the mole fractions of the components of the reducing gas, equation (10) becomes:

$$F_{O_{2m}} = \tfrac{1}{2}[F_1(X_{1H_2} + 2X_{1CH_4} - X_{1CO} - 2X_{1CO_2}) - F_3(X_{3H_2} + 2X_{3CH_4} - X_{3CO} - 2X_{3CO_2}) - 0.42 F_4 - 2F_5] \quad (11)$$

From a consideration of equation (11) it can be seen that $F_{O_{2m}}$ can be evaulated by using measurements made with the flowmeter and four gas analyzers at location "1", the flowmeter and four gas analyzers at location "3" and the flowmeters at locations "4" and "5". Since the water vapor flows $F_{1H_2O}$ and $F_{3H_2O}$ cancel out, it is necessary to make a determination of the water vapor generated in the reactor and rejected with the cooling water leaving cooler 34. This is an important advantage of the present invention because of the difficulty of measuring the water content of the gas at location "2" as pointed out above.

Since $F_{O_{2m}}$ is the rate of removal of oxygen from the ore, the aggregate amount of oxygen removed over a period of time $(O_2)r$ can be obtained by integrating $F_{O_{2m}}$ with respect to time. If the expression within the brackets in equation (11) is represented by A, then $$(O_2)r = \int_0^\theta \tfrac{1}{2} A \, d\theta \quad (12)$$

The desired variable to be used for process control purposes is the percentage reduction R which may be defined as follows:

$$R = \frac{(O_2)r}{(O_2)i} \times 100 \quad (13)$$

The initial reducible oxygen in the ore $(O_2)i$ is a constant for any given batch and may be defined as follows:

$$(O_2)i = \left[\frac{M \times 2200}{32} \times \frac{O_{2m}}{100}\right](1 - h_m) \quad (14)$$

wherein:
M = metric tons of ore charged
$O_{2m}$ = weight percent reducible oxygen in the ore
$h_m$ = humidity weight fraction of the ore
2200 = lbs./metric ton of ore
32 = molecular weight of $O_{2m}$ lbs./lb.-mole Thus $(O_2)i = 0.6875 \, M(O_{2m})(1 - h_m) \quad (15)$ Substituting (15) in (13) gives:

$$R = \left[\frac{145.45}{M(O_{2m})(1-h_m)}\right](O_2)r \qquad (16)$$

Substituting equation (12) in equation (16) gives:

$$R = \frac{72.73}{M(O_{2m})(1-h_m)} \int_0^\theta A\, d\theta \qquad (17)$$

Computer 42 can be programmed to combine the signals received from the flowmeters and gas analyzers described above, as well as inputs representing the ore charge weight, initial oxygen content and humidity fraction of the ore, in accordance with equation (17) to generate a signal representative of the percentage reduction R and this signal can be transmitted to the indicating recorder 88 to provide a visual representation of the percentage reduction. Further, it will be evident to those skilled in the art that if a measurement of the instantaneous rate of removal of oxygen is desired, either instead of or in addition to the percentage reduction measurement, computer 42 can be programmed in accordance with equation (10) above to provide a signal representative of the oxygen removal rate that is transmitted to the indicating recorder 88.

In most cases satisfactory operation of the reduction system can be achieved by using atmospheric air as the oxygen-containing gas. Under these circumstances the meters 66 and 70 can be dispensed with and a simplified form of equation (17) can be used as a basis for programming the computer 42.

For the cases where $F_5 = $ zero, equation (10) becomes:

$$F_{O_{2m}} = \tfrac{1}{2}[(F_{1H_2}-F_{3H_2}) + 2(F_{1CH_4}-F_{3CH_4}) - (F_{1CO}-F_{3CO}) - 2(F_{1CO_2}-F_{3CO_2}) - 0.42\, F_4] \qquad (18)$$

Since nitrogen does not enter into the reduction reaction and air contains 79% by volume nitrogen, a nitrogen balance between locations "1" and "3" gives:

$$F_{1N_2} + 0.79\, F_4 = F_{3N_2}$$

Solving for $F_4$:

$$F_4 = \frac{1}{0.79}(F_{3N_2} - F_{1N_2}) \qquad (19)$$

Substituting equation (19) in equation (18):

$$F_{O_{2m}} = 1/2[(F_{1H_2} - F_{3H_2}) + 2(F_{1CH_4} - F_{3CH_4}) - (F_{1CO} - F_{3CO}) - 2(F_{1CO_2} - F_{3CO_2}) + \frac{42}{79}(F_{1N_2} - F_{3N_2})] \qquad (20)$$

If X is used to represent the mole fraction of the components of the reducing gas, equation (20) becomes:

$$F_{O_{2m}} = 1/2[F_1(X_{1H_2} + 2X_{1CH_4} - X_{1CO} - X_{1CO_2} + \frac{42}{79}X_{1N_2}) - F_3(X_{3H_2} + 2X_{3CH_4} - X_{3CO} - 2X_{3CO_2} + \frac{42}{79}X_{3N_2})] \qquad (21)$$

On a dry basis the mole fraction of nitrogen may be expressed as:

$$X_{N_2} = 1 - X_{H_2} - X_{CH_4} - X_{CO} - X_{CO_2}$$

Substituting this expression for the mole fraction of nitrogen in equation (21):

$$F_{O_{2m}} = 1/2 \Big\{ F_1[X_{1H_2} + 2X_{1CH_4} - X_{1CO} - 2X_{1CO_2} + \qquad (22)$$
$$\frac{42}{79}(1 - X_{1H_2} - X_{1CH_4} - X_{1CO} - X_{1CO_2})] -$$
$$F_3[X_{3H_2} + 2X_{3CH_4} - X_{3CO} - 2X_{3CO_2} +$$
$$\frac{42}{79}(1 - X_{3H_2} - X_{3CH_4} - X_{3CO} - X_{3CO_2})] \Big\}$$

It can be seen from a consideration of equation (22) that $F_{O_{2m}}$ can be evaluated by using measurements made by the flowmeter and four analyzers at location "1" and the flowmeter and four analyzers at location "3". The flowmeters 66 and 70 are not required.

If the expression within the brackets {} in equation (22) is defined as B:

$$F_{O_{2m}} = \tfrac{1}{2} B$$

Then by analogy to equation (17) the percentage reduction R becomes:

$$R = \frac{72.73}{M(O_{2m})(1-h_m)} \int_0^\theta B\, d\theta \qquad (23)$$

Computer 42 can be programmed to combine the signals received from the flowmeters and gas analyzers with inputs representing the weight of ore charged, the initial oxygen content of the ore and the humidity fraction of the ore in accordance with equation (23) to generate a signal representative of the percent reduction R. This signal is transmitted to the indicating recorder 88 to provide a read-out of the percentage reduction.

As indicated near the beginning of the specification, in cases wherein the operating conditions are such that there is little likelihood that carburization will occur in the reduction reactor, it can be assumed that the carbon content of the reducing gas does not change during its passage through the reduction reactor and an accurate determination of percentage reduction can be obtained without measuring the reactor effluent gas flow by using a combination of three natural balances, i.e., a carbon balance as well as a hydrogen and oxygen balance.

The carbon balance may be represented as follows:

$$F_{1CO} + F_{1CO_2} + F_{1CH_4} = F_{3CO} + F_{3CO_2} + F_{3CH_4} \qquad (24)$$

If X represents the mole fractions of the gas components, then:

$$F_1(X_{1CO} + X_{1CO_2} + X_{1CH_4}) = F_3(X_{3CO} + X_{3CO_2} + X_{3CH_4}) \qquad (25)$$

Solving for $F_3$:

$$F_3 = F_1 \left( \frac{X_{1CO} + X_{1CO_2} + X_{1CH_4}}{X_{3CO} + X_{3CO_2} + X_{3CH_4}} \right) \qquad (26)$$

Substituting this value of $F_3$ in equation (22) gives:

$$F_{O_{2m}} = 1/2 \Big\{ F_1[X_{1H_2} + 2X_{1CH_4} - X_{1CO} - \qquad (27)$$

-continued $$2X_{1CO_2} + \frac{42}{79}(1 - X_{1H_2} - X_{1CH_4} - X_{1CO} -$$

$$X_{1CO_2})] - \left(\frac{X_{1CO} + X_{1CO_2} + X_{1CH_4}}{X_{3CO} + X_{3CO_2} + X_{3CH_4}}\right)[X_{3H_2} +$$

$$2X_{3CH_4} - X_{3CO} - 2X_{3CO_2} + \frac{42}{79}(1 - X_{3H_2} -$$

$$X_{3CO} - X_{3CH_4} - X_{3CO_2})]\Big\}$$

If the expression within the brackets {} in equation (27) is defined as C:

$$F_{O_{2m}} = \tfrac{1}{8} C$$

Then by analogy to equations (17) and (23) the percentage reduction R becomes:

$$R = \frac{72.73}{M(O_{2m})(1 - h_m)} \int_0^\theta C \, d\theta \qquad (28)$$

As in the case of equations (17) and (23), the computer 42 can be programmed to generate a signal representative of the percentage reduction R as defined in equation (28) using both input and effluent gas compositions but only input gas flow values. By using an embodiment of the present invention incorporating the relationship of equation (28) any errors that might arise as an incident of the measurement of effluent gas flow are eliminated and thus this approach is preferred in those cases where it can be used.

As will be evident to those skilled in the art, the method and apparatus described above can be used to measure the percentage reduction of an ore charge as it progresses through a plurality of reduction stages. The percentage reduction that has occurred in the reactor is continuously monitored so that the operator of the plant can easily detect deviations from the desired reduction pattern and take the necessary corrective action. Since a continuous record of degree of reduction is provided, the operator, as the end of a cycle approaches, can estimate whether the desired degree of metallization will be reached in a standard time interval, and if not, appropriately shorten or lengthen the reduction cycle.

It may be noted that in a system of the type described above a certain amount of reduction takes place in the cooling reactor. This cooling reactor reduction cannot usually be directly regulated by the operator. However, it has been found that if the degree of reduction of each batch is the same at the beginning of the cooling cycle, the degree of reduction of each batch at the end of the cooling cycle will be essentially the same. Thus by monitoring percentage reduction of the ore in accordance with the present method from the beginning to the end of the reduction operations, enough information is supplied to the operator to enable him to so control the operation of the system as to produce a substantially uniform product.

The method and apparatus of the invention are especially useful in cases where a product of relatively low metallization is desired. The product sponge iron is ordinarily used as a part or all of the charge to an electric arc steelmaking furnace. It has been found that in some cases economies in the overall steelmaking process can be attained by carrying out a considerable proportion of the reduction in the steel-making furnance. To achieve these advantages the reduction system is so operated as to produce a relatively heavily carburized sponge iron of say 75% to 85% metallization. Carburization of the sponge iron can be effected by carbon deposition on the sponge iron particles in the cooling reactor.

One problem encountered in this mode of operation is that when a conventional 4-reactor batch system is operated to produce a product having a low degree of metallization, the product tends to vary substantially from batch to batch. By using the present method and apparatus a more nearly uniform product can be produced from batch to batch even at metallization of say 75% to 85%.

It is, of course, to be understood that the foregoing description is illustrative only. It will be evident to those skilled in the art that numerous changes can be made in the illustrative embodiment described without departing from the spirit of the invention as defined in the appended claims.

We claim:

1. The method of determining the percentage reduction that has occurred in a reactor of a multi-stage, gaseous reduction system for reducing an oxidic metal ore to sponge metal, said system being of the type in which a reducing gas largely composed of carbon monoxide and hydrogen and which may also contain methane and carbon dioxide flows sequentially through fixed beds of metal-bearing material in a series of functionally interchangeable reactors, and the effluent gas from said beds is cooled to remove water therefrom, said method comprising the steps of (1) determining as a first value the amount of oxygen initially present in the metal-bearing bed of one of said reactors, (2) measuring the flow of reducing gas fed to said one reactor at a first location before said gas enters said reactor, (3) effectively determining the concentrations of carbon monoxide, hydrogen, methane and carbon dioxide in said reducing gas at said first location, (4) measuring the flow of effluent reducing gas from said one reactor at a second location after the effluent gas has been cooled, (5) effectively determining the concentration of carbon monoxide, hydrogen, methane and carbon dioxide in said effluent gas at said second location, (6) determining the difference between (a) the sum of the change in molar flow of hydrogen and twice the change in molar flow of methane between said two locations and (b) the sum of the change in molar flow of carbon monoxide and twice the change in molar flow of carbon dioxide between said two locations as a second value indicative of the rate of removal of oxygen from said ore, (7) integrating said second value with respect to time to obtain a third value indicative of the amount of oxygen that has been removed from the metal-bearing bed in said one reactor and (8) comparing said first and third values to obtain a fourth value indicative of the percentage reduction of the sponge metal in said one reactor.

2. The method of determining the percentage reduction of oxidic metal ores in a reactor of a gaseous reduction system of the type in which separate bodies of oxidic metal ore are simultaneously treated in a plurality of reactors to produce sponge metal, said system being of the type in which a reducing gas largely composed of carbon monoxide and hydrogen and which may also contain methane and carbon dioxide is passed through a bed of metal ore in said reactor and then cooled to remove water therefrom, said method comprising the steps of determining the concentrations of the components and flow of the gas fed to said reactor at a first location before the gas enters said reactor, determining the concentrations of the components and flow of the effluent gas from said reactor at a second location after the gas is cooled and de-watered, correlating said gas concentrations and said gas flows to obtain a first value indicative of the rate of oxygen removal from the bed of oxidic metal ore in said reactor, integrating said oxygen removal rate with respect to time to obtain a second value indicative of the aggregate amount of oxygen that has been removed from the bed of oxidic metal ore in said reactor, determining the amount of oxygen initially present in the bed of metal ore and correlating said second value with the amount of oxygen initially present in the bed of metal ore in said reactor to obtain a third value indicative of the percentage reduction of said ore.

3. The method of determining the percentage reduction that has occurred in a reactor of a multi-stage gaseous reduction system for reducing an oxidic metal ore to sponge metal, said system being of the type in which a reducing gas largely composed of carbon monoxide and hydrogen and which may also contain methane and carbon dioxide flows sequentially through fixed beds of metal-bearing material in a series of functionally interchangeable reactors, and the effluent gas from said beds is cooled to remove water therefrom, said method comprising the steps of (1) determining as a first value the amount of oxygen initially present in the metal-bearing bed of one of said reactors, (2) measuring the flow of reducing gas fed to said one reactor at a first location before said gas enters said reactor, (3) effectively determining the concentrations of carbon monoxide, hydrogen, methane and carbon dioxide in said reducing gas before said gas enters the bed of metal-bearing material in said one reactor, (4) measuring the flow of effluent reducing gas from said one reactor at a second location after the effluent gas has been cooled, (5) effectively determining the concentration of carbon monoxide, hydrogen, methane and carbon dioxide in said effluent gas at said second location, (6) incorporating said concentrations and flows in a combined hydrogen and oxygen balance to obtain a second value indicative of the rate at which oxygen is removed from the metal-bearing material in said one reactor, (7) integrating said second value with respect to time to obtain a third value indicative of the amount of oxygen that has been removed from the metal-bearing bed in said one reactor, and (8) comparing said first and third values to obtain a fourth value indicative of the percentage reduction of the sponge metal in said one reactor.

4. The method of determining the percentage reduction of iron ore in a reduction reactor of a gaseous reduction system of the type in which separate bodies of iron-bearing material are simultaneously treated in a plurality of reactors to produce sponge iron, said system being of the type in which a reducing gas largely composed of carbon monoxide and hydrogen which may also contain methane and carbon dioxide is passed through a bed of iron-bearing material in said reduction reactor and then cooled to remove water therefrom, said method comprising the steps of determining the concentrations and flow of the components of the gas fed to said reactor at a first location before the gas enters said reactor, determining the concentrations of the components of the effluent gas from said reactor at a second location after the gas is cooled and de-watered and correlating said gas concentrations and said gas flow with the quantity of oxygen initially present in said bed of iron-bearing material to obtain a signal indicative of the percentage reduction of said ore.

5. A method according to claim 4 wherein said gas concentrations and said gas flow are correlated to obtain a value indicative of the rate of oxygen removal from said bed, the removal rate is integrated with respect to time to obtain the aggregate amount of oxygen removed from said bed and said aggregate removed oxygen is correlated with the total quantity of reducible oxygen initially present in said ore to obtain said signal.

6. A method according to claim 5 wherein said gas comprises carbon monoxide, hydrogen, methane and carbon dioxide and said gas concentrations and said gas flow are correlated according to the following equation to obtain the value indicative of the rate of removal of oxygen from said bed:

$$F_{O_{2m}} = 1/2 \left\{ F_1[X_{1H_2} + 2X_{1CH_4} - X_{1CO} - 2X_{1CO_2} + \frac{42}{79}(1 - X_{1H_2} - X_{1CH_4} - X_{1CO} - X_{1CO_2})] - \left(\frac{X_{1CO} + X_{1CO_2} + X_{1CH_4}}{X_{3CO} + X_{3CO_2} + X_{3CH_4}}\right)[X_{3H_2} + 2X_{3CH_4} - X_{3CO} - 2X_{3CO_2} + \frac{42}{79}(1 - X_{3H_2} - X_{3CO} - X_{3CH_4} - X_{3CO_2})] \right\}$$

wherein $F_{O_{2m}}$ = rate of oxygen removal from the ore,
$F_1$ = total flow of gas at said first location,
$X_{1H_2}$ = mole fraction of hydrogen at said first location,
$X_{1CH_4}$ = mole fraction of methane at said first location,
$X_{1CO}$ = mole fraction of carbon monoxide at said first location,
$X_{1CO_2}$ = mole fraction of carbon dioxide at said first location,
$X_{3CO}$ = mole fraction of carbon monoxide at said second location,
$X_{3CO_2}$ = mole fraction of carbon dioxide at said second location,
$X_{3CH_4}$ = mole fraction of methane at said second location,
$X_{3H_2}$ = mole fraction of hydrogen at said second location.

7. A method according to claim 4 wherein said signal is converted into a visual representation of the percentage reduction of said ore.

8. The method of determining the percentage reduction of iron ore in a reactor of a gaseous reduction system of the type in which separate bodies of iron-bearing material are simultaneously treated in a plurality of reactors to produce sponge iron, said system being of the type in which a reducing gas largely composed of carbon monoxide and hydrogen and which may also contain methane and carbon dioxide is passed through a bed of iron-bearing material in said reactor and then cooled to remove water therefrom, said method comprising the steps of effectively measuring the concentrations of components of the gas fed to said reactor at a first location before said gas enters said reactor, measuring the flow of the feed gas at said first location, effectively measuring the concentrations of components of the effluent gas from said reactor at a second location after it is cooled and de-watered, measuring the flow of the effluent gas at said second location and correlating said gas concentrations and gas flows with the quantity of oxygen initially present in said bed of iron-bearing material to obtain a signal indicative of the percentage reduction of said ore.

9. A method according to claim 8 wherein said gas concentrations and said gas flows are correlated to obtain a value indicative of the rate of oxygen removal from said bed, the removal rate is integrated with respect to time to obtain the aggregate amount of oxygen removed from said bed and said aggregate removed oxygen is correlated with the total quantity of reducible oxygen initially present in said ore to obtain said signal.

10. A method according to claim 9 wherein said reducing gas, before it enters said reactor, is mixed with a minor amount of an oxygen-containing gas selected from air, elemental oxygen and mixtures thereof in a combustion chamber and said gas compositions and flows are correlated according to the following equation to obtain said signal indicative of the percentage reduction of said ore:

$$R = \frac{72.73}{M(O_{2m})(1-h_m)} \int_0^\theta A \, d\theta$$

wherein $A = [F_1(X_{1H_2} + 2X_{1CH_4} - X_{1CO} - 2X_{1CO_2}) - F_3(X_{3H_2} + 2B\,X_{3CH_4} - X_{3CO} - 2X_{3CO_2}) - 0.42 F_4 - 2F_5]$ R = percent reduction,
M = metric tons of ore charged to the reactor,
$O_{2m}$ = percent of reducible oxygen in the ore,
$h_m$ = humidity fraction of the ore,
$F_1$ = total flow of gas at first location,
$X_{1H_2}$ = mole fraction of hydrogen at said first location,
$X_{1CH_4}$ = mole fraction of methane at said first location,
$X_{1CO}$ = mole fraction of carbon monoxide at said first location,
$X_{1CO_2}$ = mole fraction of carbon dioxide at said first location,
$F_3$ = total flow of gas at said second location,
$X_{3H_2}$ = mole fraction of hydrogen at said second location,
$X_{3CH_4}$ = mole fraction of methane at said second location,
$X_{3CO}$ = mole fraction of carbon monoxide at said second location,
$X_{3CO_2}$ = mole fraction of carbon dioxide at said second location,
$F_4$ = flow of air to combustion chamber,
$F_5$ = flow of oxygen to combustion chamber,
$\theta$ = time.

11. A method according to claim 9 wherein said reducing gas, before it enters said reactor is mixed with a minor amount of air in a combustion chamber and said gas compositions and flows are correlated according to the following equation to obtain said signal indicative of the percentage reduction of said ore:

$$R = \frac{72.73}{M(O_{2m}(1-h_m)} \int_0^\theta B \, d\theta$$

wherein $B =$
$F_1[X_{1H_2} + 2X_{1CH_4} - X_{1CO} - 2X_{1CO_2} +$ $\frac{42}{79}(1 - X_{1H_2} - X_{1CH_4} - X_{1CO} - X_{1CO_2})] -$
$F_3[X_{3H_2} + 2X_{3CH_4} - X_{3CO} - 2X_{3CO_2} +$
$\frac{42}{79}(1 - X_{3H_2} - X_{3CH_4} - X_{3CO} - X_{3CO_2})]$ R = percent reduction,
M = metric tons of ore charged to reactor,
$O_{2m}$ = percent of reducible oxygen in the ore,
$h_m$ = humidity fraction of the ore,
$F_1$ = total flow of gas at said first location,
$X_{1H_2}$ = mole fraction of hydrogen at said first location,
$X_{1CH_4}$ = mole fraction of methane at said first location,
$X_{1CO}$ = mole fraction of carbon monoxide at said first location,
$X_{1CO_2}$ = mole fraction of carbon dioxide at said first location,
$F_3$ = total flow of gas at said second location,
$X_{3H_2}$ = mole fraction of hydrogen at said second location,
$X_{3CH_4}$ = mole fraction of methane at said second location,
$X_{3CO}$ = mole fraction of carbon monoxide at said second location,
$X_{3CO_2}$ = mole fraction of carbon dioxide at said second location,
$\theta$ = time.

12. Apparatus for determining the rate of removal of oxygen from an oxidic metal ore in a reduction reactor of a gaseous reduction system of the type in which separate bodies of metal-bearing material are simultaneously treated in a plurality of reactors to produce sponge metal, said system being of the type in which a reducing gas is heated, passed through the bed of metal-bearing material in said reduction reactor and then cooled to remove water therefrom, said apparatus comprising (a) means for measuring the flow of said gas to said reduction reactor before it is heated and for generating a signal which is a function of the measured gas flow, (b) first gas analyzer means for analyzing the gas flowing to said reduction reactor before said gas is heated and for generating signals which are functions of the concentrations of the components of said gas, (c) second gas analyzer means for analyzing the effluent gas from said reduction reactor after said gas is cooled and for generating signals which are functions of the concentrations of the components of said gas and (d) computer means responsive to each of the signals generated by means (a) through (c) for correlating said signals to obtain an output signal indicative of the rate of oxygen removal from the body of metal-bearing material in said reduction reactor and means for converting said output signal into a visual representation of the oxygen removal rate.

13. Apparatus for determining the percentage reduction of metal ore in a reduction reactor of a gaseous reduction system of the type in which separate bodies of metal-bearing material are simultaneously treated in a plurality of reactors to produce sponge metal, said system being of the type in which a reducing gas is heated, passed through the bed of metal-bearing material in said reduction reactor and then cooled to remove water therefrom, said apparatus comprising in combination with said ore reduction system (a) means for measuring the flow of said gas to said reduction reactor at a first location before said gas is heated and for generating a signal which is a function of the measured gas flow, (b) first gas analyzer means at said first location for analyzing the gas flowing to said reduction reactor before said gas is heated and for generating signals which are functions of the concentrations of the components of said gas, (c) second gas analyzer means for analyzing the effluent gas from said reactor at a second location after said gas is cooled and for generating signals which are functions of the concentration of the components of said gas and (d) computer means responsive to each of the signals generated by means (a) through (c) for (1) correlating said signals to obtain a value indicative of the rate of oxygen removal from the body of metal-bearing material in said reduction reactor, (2) integrating said removal rate with respect to time to obtain the aggregate amount of oxygen removed from said body, and (3) correlating said value of said aggregate amount with the total quantity of reducible oxygen initially present in said body of metal ore to produce a signal which is a function of the percentage reduction of said ore in said reactor.

14. Apparatus according to claim 13 wherein correlation of said signals to obtain a value indicative of the rate of oxygen removal from the body of metal-bearing material is carried out in accordance with the following equation:

$$F_{O_{2m}} = 1/2 \left\{ F_1[X_{1H_2} + 2X_{1CH_4} - X_{1CO} - 2X_{1CO_2} + \frac{42}{79}(1 - X_{1H_2} - X_{1CH_4} - X_{1CO} - X_{1CO_2})] - \left(\frac{X_{1CO} + X_{1CO_2} + X_{1CH_4}}{X_{3CO} + X_{3CO_2} + X_{3CH_4}}\right)[X_{3H_2} + 2X_{3CH_4} - X_{3CO} - 2X_{3CO_2} + \frac{42}{79}(1 - X_{3H_2} - X_{3CO} - X_{3CH_4} - X_{3CO_2})] \right\}$$

wherein $F_{O_{2m}}$ = rate of oxygen removal from the ore,
$F_1$ = total flow of gas at said first location,
$X_{1H_2}$ = mole fraction of hydrogen at said first location,
$X_{1CH_4}$ = mole fraction of methane at said first location,
$X_{1CO}$ = mole fraction of carbon monoxide at said first location,
$X_{1CO_2}$ = mole fraction of carbon dioxide at said first location,
$X_{3CO}$ = mole fraction of carbon monoxide at said second location,
$X_{3CO_2}$ = mole fraction of carbon dioxide at said second location,
$X_{3CH_4}$ = mole fraction of methane at said second location,
$X_{3H_2}$ = mole fraction of hydrogen at said second location.

15. Apparatus for determining the percentage reduction of metal ore in a reduction reactor of a gaseous reduction system of the type in which separate bodies of metal-bearing material are simultaneously treated in a plurality of reactors to produce sponge metal, said system being of the type in which a reducing gas is heated, passed through the bed of metal-bearing material in said reduction reactor and then cooled to remove water therefrom, said apparatus comprising in combination with said ore reduction system (a) a meter for measuring the flow of said gas to said reduction reactor at a first location before said gas is heated and for generating a singal which is a function of the measured gas flow, (b) first gas analyzer means for analyzing the gas flowing to said reduction reactor at a first location before said gas is heated and for generating signals which are functions of the concentrations of the components of said gas, (c) a meter for measuring the flow of effluent gas from said reactor at a second location after said gas is cooled and for generating a signal which is a function of the measured gas flow, (d) second gas analyzer means for analyzing the effluent gas from said reactor at a second location after said gas is cooled and for generating signals which are functions of the concentrations of the components of said gas, (e) computer means responsive to each of the signals generated by means (a) through (d) for (1) correlating said signals to obtain a value indicative of the rate of oxygen removal from the body of metal-bearing material in said reduction reactor, (2) integrating said removal rate with respect to time to obtain the aggregate amount of oxygen removed from said body, and (3) correlating said value of said aggregate amount with the total quantity of reducible oxygen initially present in said body of metal ore to produce a signal which is a function of the percentage reduction of said ore in said reactor and (f) indicating means actuated by said computer output signal to indicate said percentage reduction.

16. Apparatus for determining the percentage reduction of metal ore in a reduction reactor of a gaseous reduction system of the type in which separate bodies of metal-bearing material are simultaneously treated in a plurality of reactors to produce sponge metal, said system being of the type in which a reducing gas largely composed of carbon monoxide, hydrogen, methane and carbon dioxide is heated to an elevated temperature, mixed with a minor amount of oxygen-containing gas selected from air, oxygen and mixtures thereof in a combustion chamber, passed through the bed of metal-bearing material in said reduction reactor and then cooled to remove water therefrom, said apparatus comprising in combination with said ore reduction system (a) means for measuring the flow of said gas to said reduction reactor at a first location before it is heated and for generating a signal which is a function of the thus measured gas flow, (b) first gas analyzer means at said first location for analyzing the carbon monoxide, hydrogen, methane and carbon dioxide content of the gas flowing to said reduction reactor before it is heated and for generating signals that are functions of the concentrations of each of said gaseous components, (c) means for measuring the flow of oxygen-containing gas to said combustion chamber and for generating a signal which is a function of said gas flow, (d) means for measuring the flow of effluent gas from said reactor at a second location after it is cooled and for generating a signal which is a function of the thus measured gas flow, (e) second gas analyzer means at said second location for analyzing the carbon monoxide, hydrogen, methane and carbon dioxide content of the effluent gas from said reactor after it is cooled and for generating signals which are functions of the concentration of each of said gaseous components and (f) computer means responsive to each of the signals generated by means (a) through (e) for producing a signal that is a function of the percentage reduction of said ore in said reactor by correlating said signals with the total quantity of reducible oxygen initially present in said body of ore in accordance with the following equation:

$$R = \frac{72.73}{M(O_{2m})(1 - h_m)} \int_0^\theta A \, d\theta$$

wherein $A = [F_1(X_{1H_2} + 2X_{1CH_4} - X_{1CO} - 2X_{1CO_2}) - F_3(X_{3H_2} + 2X_{3CH_4} - X_{3CO} - 2X_{3CO_2}) - 0.42 F_4 - 2F_5]$ $R$ = percent reduction,
$M$ = metric tons of ore charged to reactor,
$O_{2m}$ = percent of reducible oxygen in the ore,
$h_m$ = humidity fraction of the ore,
$F_1$ = total flow of gas at said first location,
$X_{1H_2}$ = mole fraction of hydrogen at said first location,
$X_{1CH_4}$ = mole fraction of methane at said first location,
$X_{1CO}$ = mole fraction of carbon monoxide at said first location,
$X_{1CO_2}$ = mole fraction of carbon dioxide at said first location,
$F_3$ = total flow of gas at said second location,
$X_{3H_2}$ = mole fraction of hydrogen at said second location,
$X_{3CH_4}$ = mole fraction of methane at said second location,
$X_{3CO}$ = mole fraction of carbon monoxide at said second location,
$X_{3CO_2}$ = mole fraction of carbon dioxide at said second location,
$F_4$ = flow of air to combustion chamber,
$F_5$ = flow of oxygen to combustion chamber,
$\theta$ = time.

17. Apparatus for determinging the percentage reduction of metal ore in a reduction reactor of a gaseous reduction system of the type in which separate bodies of metal-bearing material are simultaneously treated in a plurality of reactors to produce sponge metal, said system being of the type in which a reducing gas largely composed of carbon monoxide, hydrogen, methane and carbon dioxide is heated, mixed with a minor amount of air in a combustion chamber, passed through the bed of metal-bearing material in said reduction reactor and then cooled to remove water therefrom, said apparatus comprising in combination with said ore reduction system (a) means for measuring the flow of said gas to said reduction reactor at a first location before it is heated and for generating a signal which is a function of the measured gas flow, (b) first gas analyzer means at said first location for analyzing the carbon monoxide, hydrogen, methane and carbon dioxide content of the gas flowing to said reduction reactor before it is heated and for generating signals that are functions of the concentrations of each of said gaseous compounds, (c) means for measuring the flow of effluent gas from said reactor at a second location after it is cooled and for generating a signal which is a function of the measured gas flow, (d) second gas analyzer means at said second location for analyzing the carbon monoxide, hydrogen, methane and carbon dioxide content of the effluent gas from said reactor after it is cooled and for generating signals which are functions of the concentration of each of said gaseous components, and (e) computer means responsive to each of the signals generated by means (a) through (d) for producing a signal that is a function of the percentage reduction of said ore in said reactor by correlating said signals with the total quantity of reducible oxygen initially present in said body of ore in accordance with the following equation:

$$R = \frac{72.73}{M(O_{2m}(1 - h_m)} \int_0^\theta B \, d\theta$$

wherein $B =$
$F_1[X_{1H_2} + 2X_{1CH_4} - X_{1CO} - 2X_{1CO_2} + \frac{42}{79}(1 - X_{1H_2} - X_{1CH_4} - X_{1CO} - X_{1CO_2})] -$
$F_3[X_{3H_2} + 2X_{3CH_4} - X_{3CO} - 2X_{3CO_2} + \frac{42}{79}(1 - X_{3H_2} - X_{3CH_4} - X_{3CO} - X_{3CO_2})]$ $R$ = percent reduction,
$M$ = metric ions of ore charged to the reactor,
$O_{2m}$ = percent of reducible oxygen in the ore,
$h_m$ = humidity fraction of the ore,
$F_1$ = total flow of gas at said first location,
$X_{1H_2}$ = mole fraction of hydrogen at said first location,
$X_{1CH_4}$ = mole fraction of methane at said first location,
$X_{1CO}$ = mole fraction of carbon monoxide at said first location,
$X_{1CO_2}$ = mole fraction of carbon dioxide at said first location,
$F_3$ = total flow of gas at said second location,
$X_{3H_2}$ = mole fraction of hydrogen at said second location,
$X_{3CH_4}$ = mole fraction of methane at said second location,
$X_{3CO}$ = mole fraction of carbon monoxide at said second location,
$X_{3CO_2}$ = mole fraction of carbon dioxide at said second location,
$\theta$ = time.

18. The method of determining the percentage reduction of iron ore in a reduction reactor of a gaseous reduction system of the type in which separate bodies of iron-bearing material are simultaneously treated in a plurality of reactors to produce sponge iron, said system being of the type in which a reducing gas largely composed of carbon monoxide and hydrogen and which may also contain methane and carbon dioxide is passed through a bed of iron-bearing material in said reactor and then cooled to remove water therefrom, said reducing gas, before it enters said reactor, being mixed in a combustion chamber with a minor amount of an oxygen-containing gas selected from air, elemental oxygen and mixtures thereof, said method comprising the steps of determining the concentrations of components of the gas fed to said reactor at a first location before said gas enters said reactor, measuring the flow of feed gas at said first location, measuring the flow of oxygen-containing gas mixed with said reducing gas, determining the concentrations of components of the effluent gas from said reactor at a second location after it is cooled and dewatered, measuring the flow of effluent gas at said second location and correlating said concentrations and gas flows with the quantity of oxygen initially present in said bed of iron-bearing material to obtain a signal indicative of the percentage reduction of said ore.

19. The method of determining the percentage reduction that has occurred in a reactor of a multi-stage gaseous reduction system for reducing an oxidic metal ore to sponge metal, said system being of the type in which a reducing gas largely composed of carbon monoxide and hydrogen and which may also contain methane and carbon dioxide flows sequentially through fixed beds of metal-bearing material in a series of functionally interchangeable reactors, and the effluent gas from said beds is cooled to remove water therefrom, said method comprising the steps of (1) determining as a first value the amount of oxygen initially present in the metal-bearing bed of one of said reactors, (2) measuring the flow of reducing gas fed to said one reactor at a first location before said gas enters said reactor, (3) effectively determining the concentrations of carbon monoxide, hydrogen, methane and carbon dioxide in said reducing gas at said first location, (4) measuring the flow of effluent reducing gas from said one reactor at a second location after the effluent gas has been cooled, (5) effectively determining the concentration of carbon monoxide, hydrogen, methane and carbon dioxide in said effluent gas at said second location, (6) incorporating said concentrations and flows in a combined hydrogen and oxygen balance to obtain a second value indicative of the rate at which oxygen is removed from the metal-bearing material in said one reactor, (7) integrating said second value with respect to time to obtain a third value indicative of the amount of oxygen that has been removed from the metal-bearing bed in said one reactor, and (8) comparing said first and third values to obtain a fourth value indicative of the percentage reduction of the sponge metal in said one reactor.

20. The method of determining the percentage reduction that has occurred in a reduction reactor of a multistage gaseous reduction system for reducing an oxidic metal ore to sponge metal, said system being of the type in which a reducing gas largely composed of carbon monoxide and hydrogen and which may also contain methane and carbon dioxide flows sequentially through fixed beds of metal-bearing material in a series of functionally interchangeable reactors and the effluent gas from said beds is cooled to remove water therefrom, said method comprising the steps of (1) determining as a first value the amount of oxygen initially present in the metal-bearing bed of one of said reactors, (2) measuring the flow of reducing gas fed to said one reactor at a first location before said gas enters said reactor, (3) effectively determining the concentrations of carbon monoxide, hydrogen, methane and carbon dioxide in said reducing gas at said first location, (4) effectively determining the concentration of carbon monoxide, hydrogen, methane and carbon dioxide in said effluent gas at a second location after the gas is cooled and dewatered, (5) incorporating said concentrations and flow in a combined hydrogen, oxygen and carbon balance to obtain a second value indicative of the rate at which oxygen is removed from the metal-bearing bed in said one reactor, (6) integrating said second value with respect to time to obtain a third value indicative of the amount of oxygen that has been removed from the metal-bearing bed in said one reactor and (7) comparing said first and third values to obtain a fourth value indicative of the percentage reduction of the sponge metal in said one reactor.

21. The method of determining the percentage reduction of iron ore in a reduction reactor of a gaseous reduction system of the type in which separate bodies of iron-bearing material are simultaneously treated in a plurality of reactors to produce sponge iron, said system being of the type in which a reducing gas largely composed of carbon monoxide and hydrogen and which may also contain methane and carbon dioxide is passed through a bed of iron-bearing material in said reduction reactor and then cooled to remove water therefrom, said method comprising the steps of determining the concentrations of the components of the gas fed to said reactor at a first location before the gas enters said bed of iron-bearing material, determining the concentrations of the components of the effluent gas from said reactor at a second location after the gas is cooled and de-watered, effectively measuring the flow of gas through said reactor, and correlating said gas concentrations and said gas flow with the quantity of oxygen initially present in said bed of iron-bearing material to obtain a signal indicative of the percentage reduction of said ore.

* * * * *

UNITED STATES PATENT AND TRADEMARK OFFICE
CERTIFICATE OF CORRECTION

PATENT NO. : 4,121,922
DATED : October 24, 1978
INVENTOR(S) : Patrick W. MacKay et al.

It is certified that error appears in the above–identified patent and that said Letters Patent are hereby corrected as shown below:

Claim 10, column 15, line 30, omit "B"

Claim 17, column 19, line 35, "determinging" should be --determining--.

Signed and Sealed this

Sixth Day of February 1979

[SEAL]

Attest:

RUTH C. MASON
Attesting Officer

DONALD W. BANNER
Commissioner of Patents and Trademarks